United States Patent
Voegele et al.

(10) Patent No.: US 7,946,453 B2
(45) Date of Patent: May 24, 2011

(54) SURGICAL BAND FLUID MEDIA DISPENSER

(75) Inventors: James W. Voegele, Cincinnati, OH (US); John V. Hunt, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1157 days.

(21) Appl. No.: 11/558,107

(22) Filed: Nov. 9, 2006

(65) Prior Publication Data

US 2008/0114315 A1    May 15, 2008

(51) Int. Cl.
*B67D 7/78* (2010.01)
*A61B 17/00* (2006.01)
*A61M 5/00* (2006.01)

(52) U.S. Cl. .......................... 222/134; 606/213; 604/187

(58) Field of Classification Search .................. 604/186, 604/207, 224, 311; 640/81, 82, 187, 191, 640/227, 236, 238, 246, 249; 222/134; 606/213
See application file for complete search history.

(56) References Cited

U.S. PATENT DOCUMENTS

| | | | |
|---|---|---|---|
| 3,110,310 A * | 11/1963 | Cislak | 604/209 |
| 5,971,951 A * | 10/1999 | Ruskewicz | 604/62 |
| 6,016,800 A * | 1/2000 | Century | 128/200.22 |
| 6,340,097 B1 | 1/2002 | D'Alessio et al. | |
| 2003/0015195 A1 * | 1/2003 | Haaije de Boer et al. | 128/203.15 |
| 2003/0044219 A1 | 3/2003 | Quintero | |
| 2004/0190975 A1 | 9/2004 | Goodman et al. | |
| 2005/0175395 A1 * | 8/2005 | Quintero et al. | 401/133 |

* cited by examiner

*Primary Examiner* — Kevin C Sirmons
*Assistant Examiner* — William Carpenter
(74) *Attorney, Agent, or Firm* — Frost Brown Todd LLC (57) ABSTRACT

A multiple use fluid dispenser dispenses a flowable material in a precise pattern and quantity with leaking and clogging between dispensing avoided by employing a trigger fired syringe plunger to expel a fixed volume through a band. Between strokes, an advancement knob rotates the band over a distal dispensing tip to a nondispensing location that wipes excess flowable material and seals a dispensing orifice in a fluid conduit. The advancement knob further may rotate the band to a dispensing position wherein a combination of one or more dispensing holes produce a desired pattern and rate of flow with material over the dispensing hole(s) serving to initiate the flowable material, to control placement, serve as a detachable bandage or buttress material, etc.

14 Claims, 12 Drawing Sheets

FIG. 12 she# SURGICAL BAND FLUID MEDIA DISPENSER

CROSS REFERENCE TO RELATED APPLICATIONS

The present application is related to commonly owned U.S. patent application Ser. No. 11/558,138, "SURGICAL MULTIPLE USE ADHESIVE APPLIER", to Sheets et al., filed on even date herewith, the disclosure of which is hereby incorporated by reference in its entirety.

FIELD OF THE INVENTION

This invention relates to surgical dispensers of flowable material onto tissue with precise placement at a precise volume without leaking or clogging before or between uses for open and/or minimally invasive surgical procedures for purposes such as applying sealants, adhesives, drugs, schlerosing/necrosing agents, etc.

BACKGROUND OF THE INVENTION

Numerous swabs, applicators, dispensers and kits for dispensing and applying various materials, including adhesive materials, are known. However, these known arrangements possess various shortcomings that make them undesirable in many applications.

Monomer and polymer adhesives are used in both industrial (including household) and medical applications. Included among these adhesives are the 1,1-disubstituted ethylene monomers and polymers, such as the X-cyanoacrylates. Since the discovery of the adhesive properties of such monomers and polymers, they have found wide use due to the speed with which they cure, the strength of the resulting bond formed, and their relative ease of use. These characteristics have made the .alpha.-cyanoacrylate adhesives the primary choice for numerous applications such as bonding plastics, rubbers, glass, metals, wood, and, more recently, biological tissues.

Medical applications of 1,1-disubstituted ethylene monomer adhesive compositions include use as an alternative or an adjunct to surgical sutures and staples in wound closure as well as for covering and protecting tissue wounds such as lacerations, abrasions, burns, stomatitis, sores, and other open surface wounds. When such an adhesive is applied, it is usually applied in its monomeric form, and the resultant polymerization gives rise to the desired adhesive bond.
Applicators for Dispensing a Polymerizable and/or Cross-Linkable Material, such as a 1,1-disubstituted Ethylene Formulation.

In general, many different 1,1-disubstituted ethylene formulations are known for various applications, for example, cyanoacrylate formulations used as fast-acting surgical adhesives, sealants, bioactive agent release matrixes and implants utilized in medical, surgical and other in vivo applications.

However, due to the need to apply the adhesive in its monomeric form, and due to the rapid polymerization rate of the monomers, it has been very difficult to design effective and commercially viable applicators and/or dispensers. Such applicators and/or dispensers must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained. This latter requirement, that the actual or perceived sanitary and sterile condition of the monomer and applicator be maintained, is particularly important in medical applications, where the user and/or the patient desires a clean product so as not to introduce further bacteria or foreign matter into a wound site.

While such adhesives have very demanding properties (e.g., rapid polymerization) that impede desired dispensing, other liquids to varying degrees have similar limitations that would benefit from precise placement without clogging and leaking, especially for a device capable of multiple uses. Consequently, a significant need exists for an improved surgical fluid dispenser.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
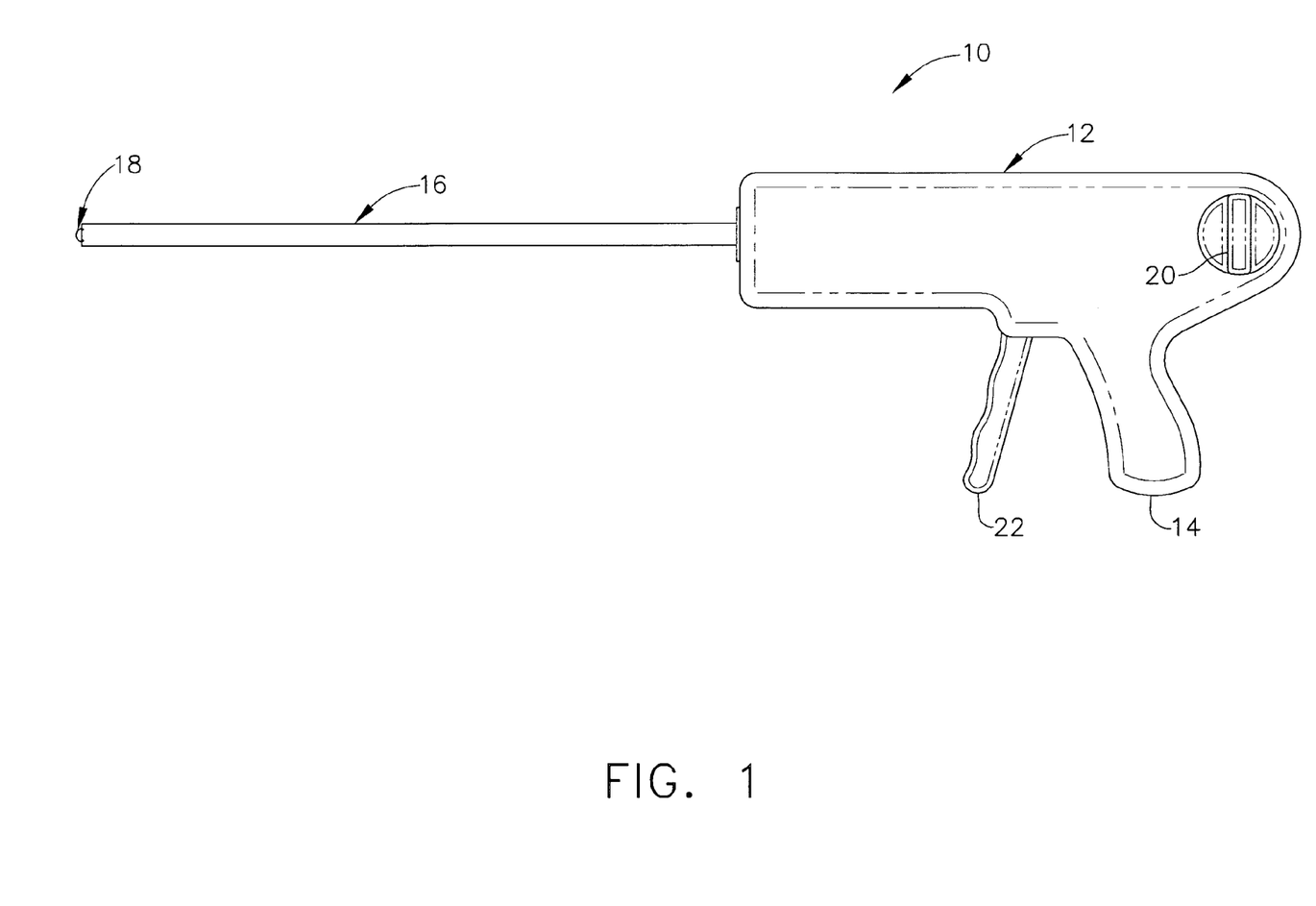
FIG. 1 is a left side view in elevation of a multiple use fluid dispenser for surgical use.
Figure 2:
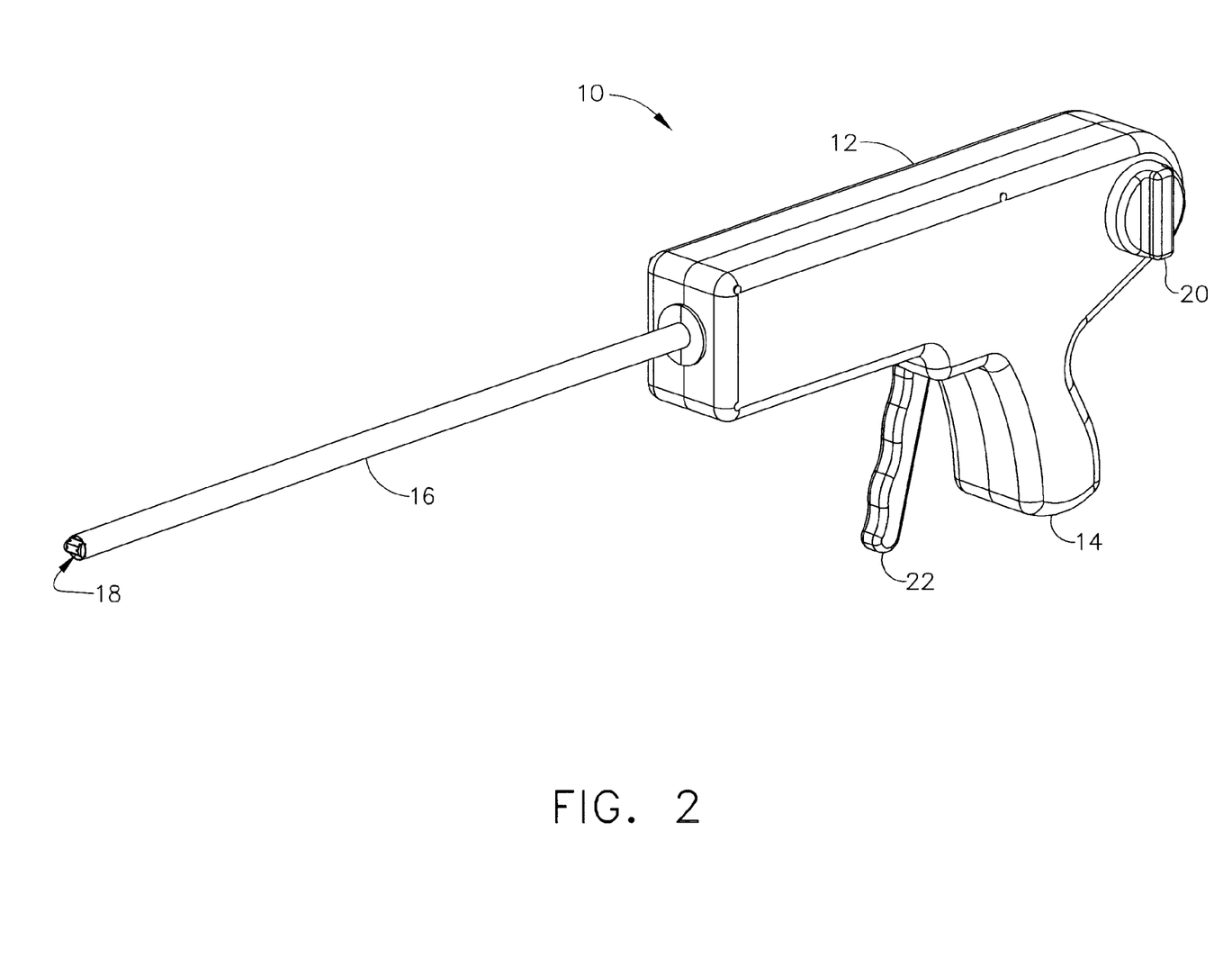
FIG. 2 is a front left isometric view of the multiple use fluid dispenser of FIG. 1.

Turning to the Figures, wherein like numerals denote like components throughout the several views, in FIGS. 1-2, a multiple use fluid dispenser 10 applies a discrete, precise volume of a medically therapeutic flowable material (e.g., adhesive, sealant, drug, schlerosing/necrosing agent, etc.) without leaking or clogging before or between uses. A handle 12 includes a pistol grip 14 that is held by the surgeon for positioning an elongate shaft 16 to position a distal applicator tip 18 to a desired location as part of a topical, open or minimally invasive (e.g., laparoscopic, endoscopic) surgical procedure. Positioning an advancement knob 20 prepares the distal applicator tip 18 for the next dispensing application. Then, depression of a trigger 22 proximally toward the pistol grip 14 causes the dispensing application. The advancement knob 20 may then be turned to a next position to prevent leaking or clogging between dispensing operations.

Figure 3:
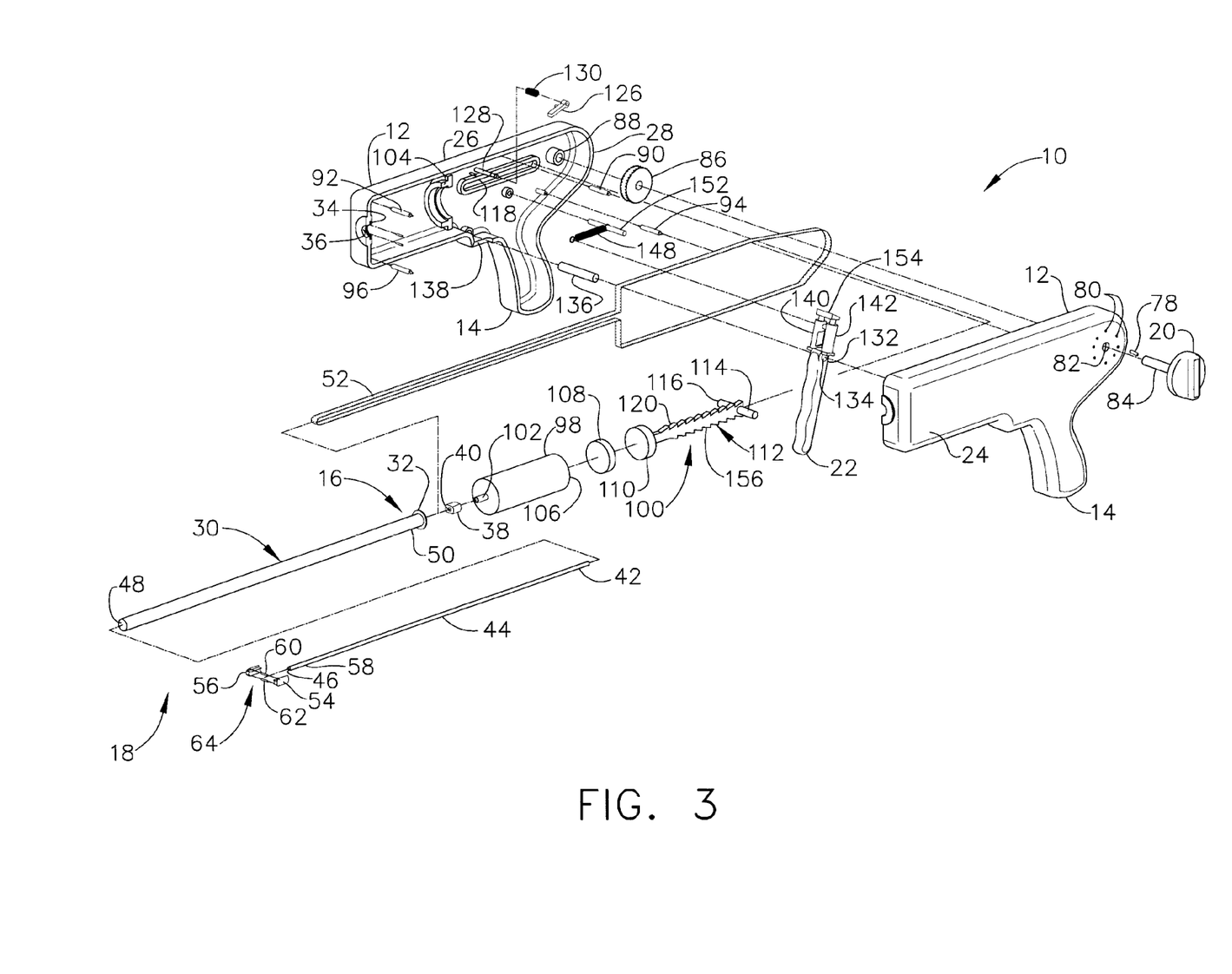
FIG. 3 is a front left exploded view of the multiple use fluid dispenser of FIG. 1.
Figure 4:
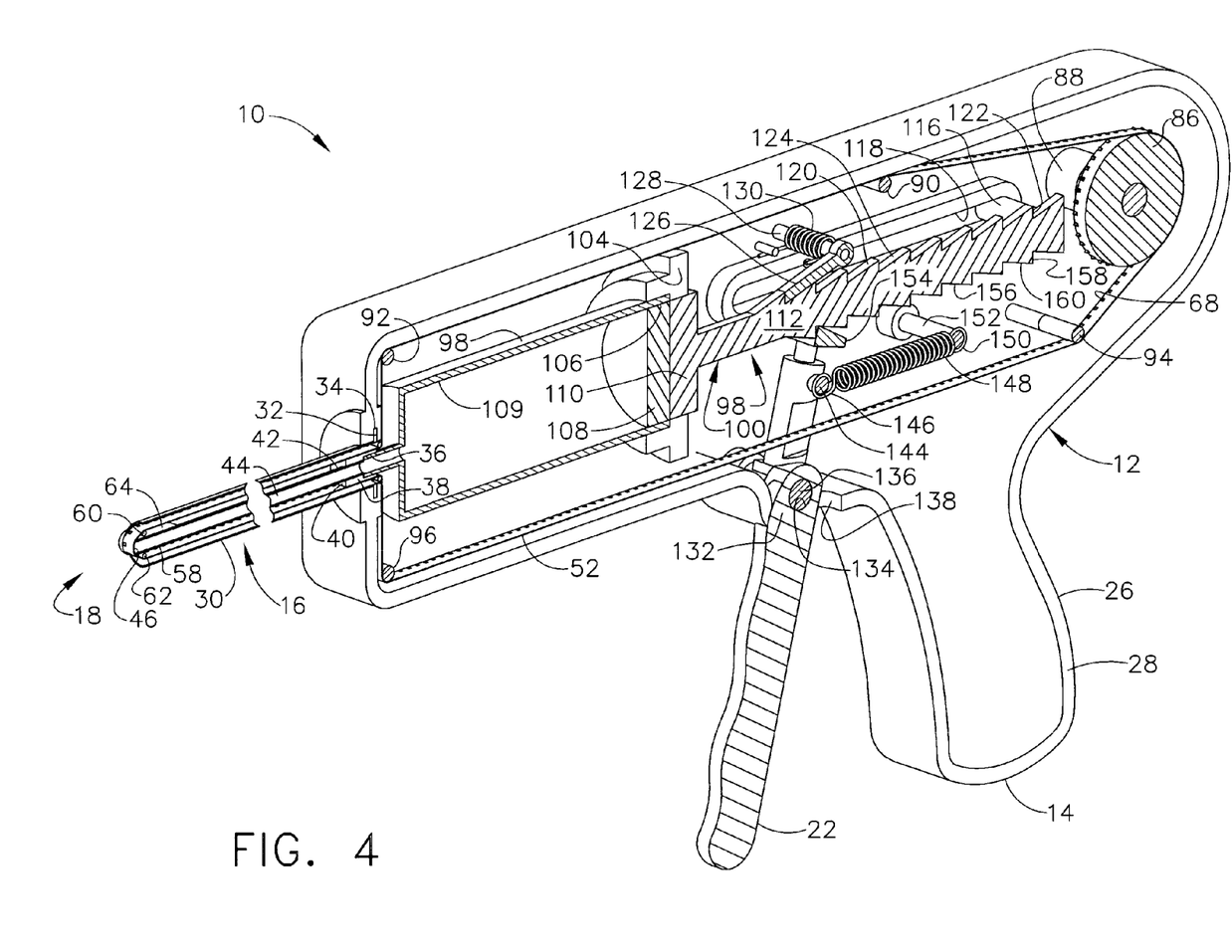
FIG. 4 is a front left isometric view of the multiple use fluid dispenser of FIG. 1 taken in vertical cross section along a longitudinal axis and with a portion of the elongate shaft omitted.

In FIGS. 3-4, the housing 12 of the multiple use fluid dispenser 10 has left and right housing half shells 24, 26 that are generally laterally symmetric and fused along a seam 28. The elongate shaft 16, which includes an outer tube 30 with a proximal disk flange 32 extending outwardly, is engaged within a respective internal slot 34 surrounding a half circular hole 36 formed on a distal end of each housing half shell 24, 26.

A coupling member 38 has a longitudinal through hole 40 to receive a proximal end 42 of narrow diameter fluid conduit 44 that is received within the outer tube 30 distally terminating in a dispensing orifice 46 at an open distal end 48 of the outer tube 30 at the distal applicator tip 18. The coupling member 38 is laterally sized for engaging an inner diameter at a proximal end 50 of the outer tube 30 and vertically narrowed to leave room for a band 52 to pass around the coupling member 38 and the fluid conduit 44. Laterally symmetric left and right tip supports 54, 56 are attached to each side of a distal end 58 of the fluid conduit 44, supporting therebetween a top transverse roller 60 and a bottom transverse roller 62 that reside respectively above and below the fluid conduit 44 within the outer tube 30. The assembled tip supports 54, 56 and rollers 60, 62 form a distal spacer 64 that contacts an inner diameter of the open distal end 48 of the outer tube 30 and is vertically narrowed to allow the band 52 to pass around the rollers 60, 62 and pass closely over the dispensing orifice 46 of the fluid conduit 44.

Figure 5:
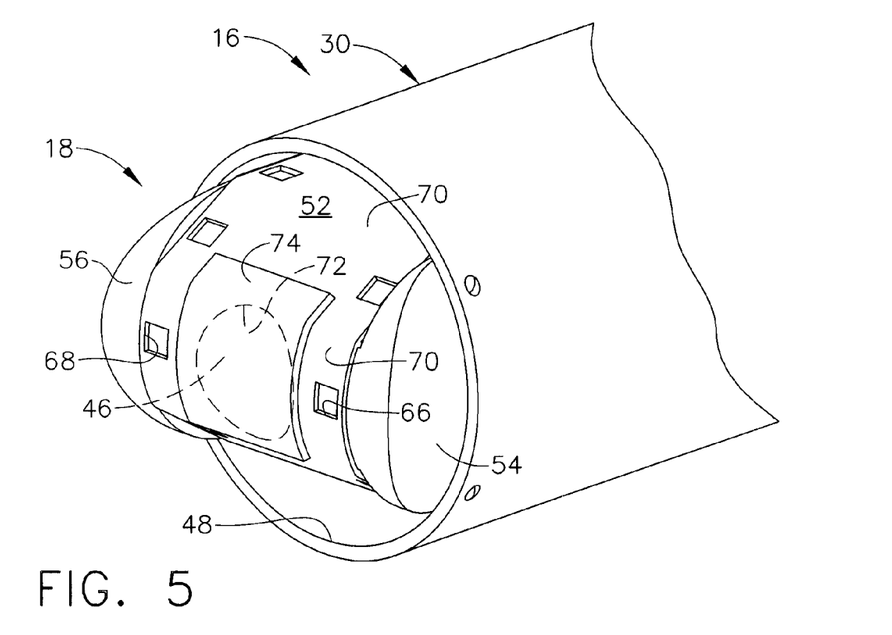
FIG. 5 is a front left isometric detail view of a distal applicator tip of the multiple use fluid dispenser of FIG. 1.
Figure 6:
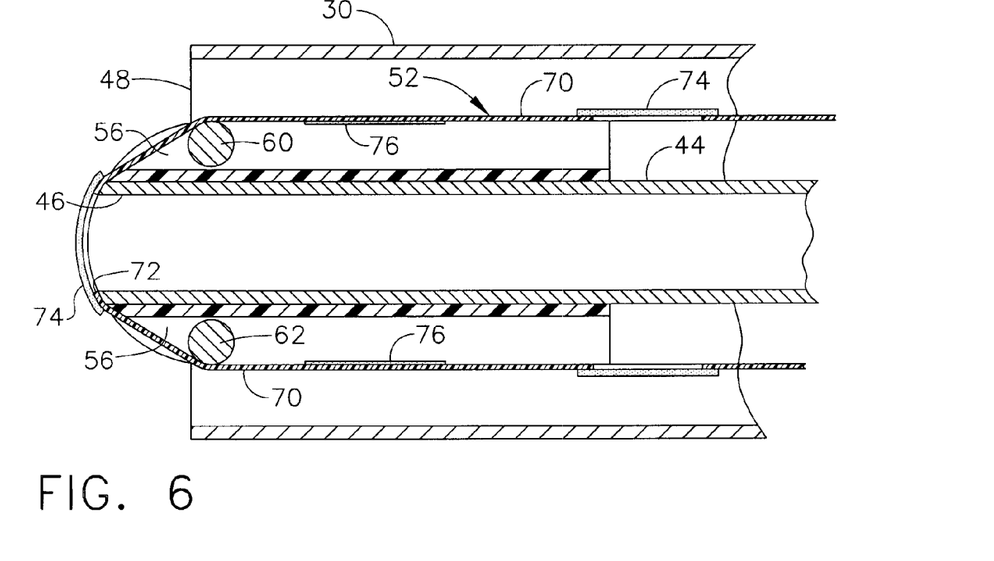
FIG. 6 is a left side view in vertical cross section taken through a longitudinal axis of the distal applicator tip of FIG. 5.

In FIGS. 5-6, the band 52 is depicted as having left and right series of sprocket holes 66, 68 formed in a band substrate 70 similar to those formed in celluloid movie film. Intermittent center openings, depicted as circular holes 72 are formed in the band substrate 70 for being aligned with the dispensing orifice 46 of the fluid conduit 44 for dispensing the flowable material. An outer band layer, depicted as an outer rectangular patch 74, is attached to the band substrate 72 and sized and positioned to surround the circular hole 72. The outer rectangular patch 74 may be detachable, such as due to the flexure and friction by contact to tissue, by the chemical composition of the flowable material, and/or the fluid pressure imparted to an inner surface of the rectangular patch 74. The detached patch 74 may serve as a bandage or buttress. Alternatively, the rectangular patch 74 may be permanently attached to the band substrate 70, serving as a mesh to diffuse the dispensing of flowable material, serving to impart an activation compound to initiate polymerization, etc. In FIG. 6, the band 52 also includes an inner band layer, depicted as an inner rectangular patch 76, are attached to an inner surface of the band substrate 70 spaced in between circular holes 72. The inner rectangular patch 76 may serve to prevent leakage between dispensing, may prevent air and/or activation compounds from contacting the dispensing orifice 46 of the fluid conduit 44 to reduce or avoid clogging, may wipe the dispensing orifice 46, etc.

Returning to FIGS. 3-4, the advancement knob 20 presented on the right, aft side of the handle 12 positions the band 52 to present these surfaces to the dispensing orifice 46 by having an indexing pin 78 that engages a series of radially spaced detents 80 which are formed on an exterior of the housing 12 around a shaft hole 82 on the right housing half shell 24. A rightward advancement shaft 84 attached to the advancement knob 20 passes through the shaft hole 82 and is centrally engaged to a sprocket 86 and then rotatingly received within a cylindrical receptacle 88 presented by the left housing half shell 24. The sprocket 86 engages the sprocket holes 66, 68 of the band 52 that passes approximately over an aft portion of a circumference of the sprocket 86. A top portion of the band 52 goes forward from a top surface of the sprocket 86 into a close spacing between a laterally positioned top guide pin 90 below the top seam 28 of the housing 12 and then around a front top guide pin 92 and down to bend into the spacing above the coupling member 38 and then distally. A bottom portion of the band 52 goes down and forward from the sprocket 86 around a bottom aft guide pin 94 and forward around a front bottom guide pin 96 and up to bend forward below the coupling member 38 and then distally.

Fluid dispensing is provided by a syringe 97 formed by a syringe barrel 98 and a plunger 100. A distal nozzle 102 of the syringe barrel 98 is sized to be received proximally into the longitudinal through hole 40 of the coupling member 38, held therein by a circular boss 104 formed on both housing half shells 24, 26 to engage a proximal opening 106 of the syringe barrel 98. The plunger 100 has a distal cylindrical plunger seal 108 that dynamically seals to an inner diameter of the syringe barrel 98 defining a syringe volume 109 containing flowable material and is positioned along a longitudinal axis defined by the syringe barrel 98 and fluid conduit 44 by a distal disk face 110 of a ratcheting plunger arm 112, which proximally terminates in left and right lateral pins 114, 116 that longitudinally translate in a longitudinal track 118 formed on an interior of both handle half shells 24, 26. An upper rack 120 formed into the ratcheting plunger arm 112 with proximally directed tooth vertical faces 122 between ramp surfaces 124 makes ratcheting engagement with a distally directed anti-backup pawl 126 pivoting about a pawl pin 128 between the half shells 24, 26 and biased downward into engagement by a torsion spring 130 received on a right side of the pawl pin 128.

A top end 132 of the trigger 22 has a pivot hole 134 that is rotatably received upon a trigger axle 136 that passes laterally within a trigger aperture 138 formed on an undersurface of the housing 12 distal to the pistol grip 14. A right post 140 is attached to the top end 132 of the trigger 22 extending upwardly within the housing to the right side of the band 52. A left post 142 is assembled onto the top end 132 of the trigger 22 to the left of the band 52. A spring mounting 144 extends laterally between the right and left posts 140, 142 to receive a distal end 146 of a compression spring 148. A proximal end 150 of the compression spring 148 is received upon a lateral spring pin 152 extending between the half shells 24, 26. A ratchet cam member 154 mounts on top of the posts 140, 142 and engages a lower rack 156 formed into a lower surface of the ratcheting plunger arm 112 with proximally directed tooth vertical faces 158 between ramp surfaces 160.

It should be appreciated with the benefit of the present disclosure that an anti-backup mechanism and a trigger may utilize the same ratcheting rack segment in applications consistent with the present invention. In addition, rather than gear type engagement, a rod-binding engagement may be employed in applications consistent with the present invention, similar to caulking guns.

Figure 7:
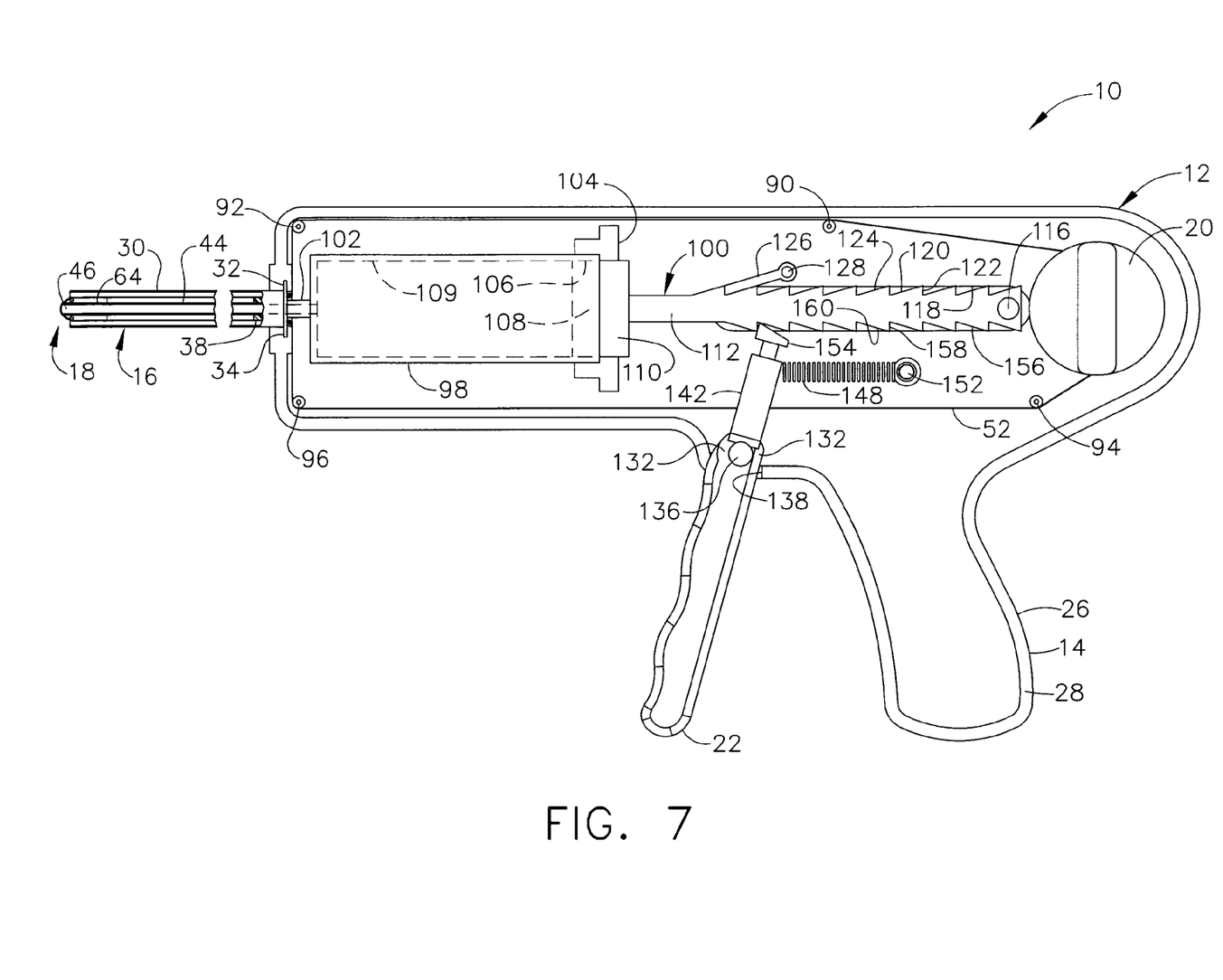
FIG. 7 is a left side view in elevation of the multiple use fluid dispenser of FIG. 1 with a left housing half shell and a left portion of the shaft removed in an initial state with a trigger forward and a syringe plunger fully retracted aft.

In use, in FIG. 7 the multiple use fluid dispenser 10 is in an initial state with the syringe volume 109 fully filled and the plunger 100 fully retracted. The cam member 154 is engaged to a distal most position on the lower rack 156 with the trigger 22 fully forward under the biasing of the compression spring 148. The plunger seal 108 is prevented from backing out of the syringe barrel 98 by the lateral pins 114, 116 of the plunger arm 112 residing within a proximal end of the longitudinal track 118 in the housing 12 as well as by the anti-backup pawl 126 engaged to a distal most position on the upper rack 120. The advancement knob 20 has already rotated the band 52 into a dispensing position.

Figure 8:
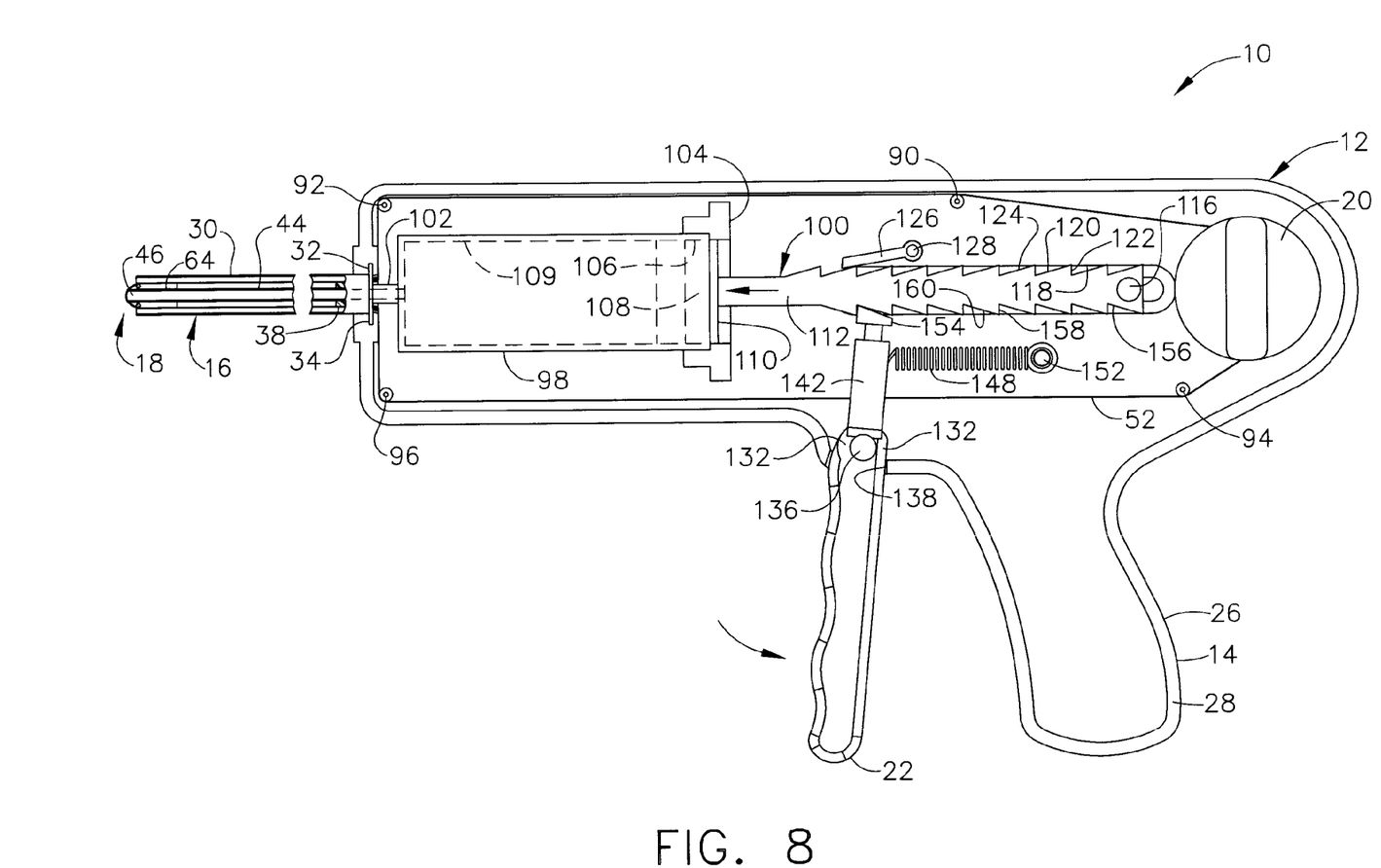
FIG. 8 is a left side view in elevation of the multiple use fluid dispenser of FIG. 1 with the left housing half shell and portions of the shaft removed during a first dispensing stroke of the trigger.

In FIG. 8, the trigger 22 is being depressed aft toward the pistol grip 14 stretching the compression spring 148, distally advancing the cam member and thus the ratcheting plunger arm 112. The anti-backup pawl 126 rides overtop of the upper rack 120. The distal movement of the plunger seal 108 forces a displaced volume of flowable material within the syringe volume 109 out of the distal dispensing tip 18.

Figure 9:
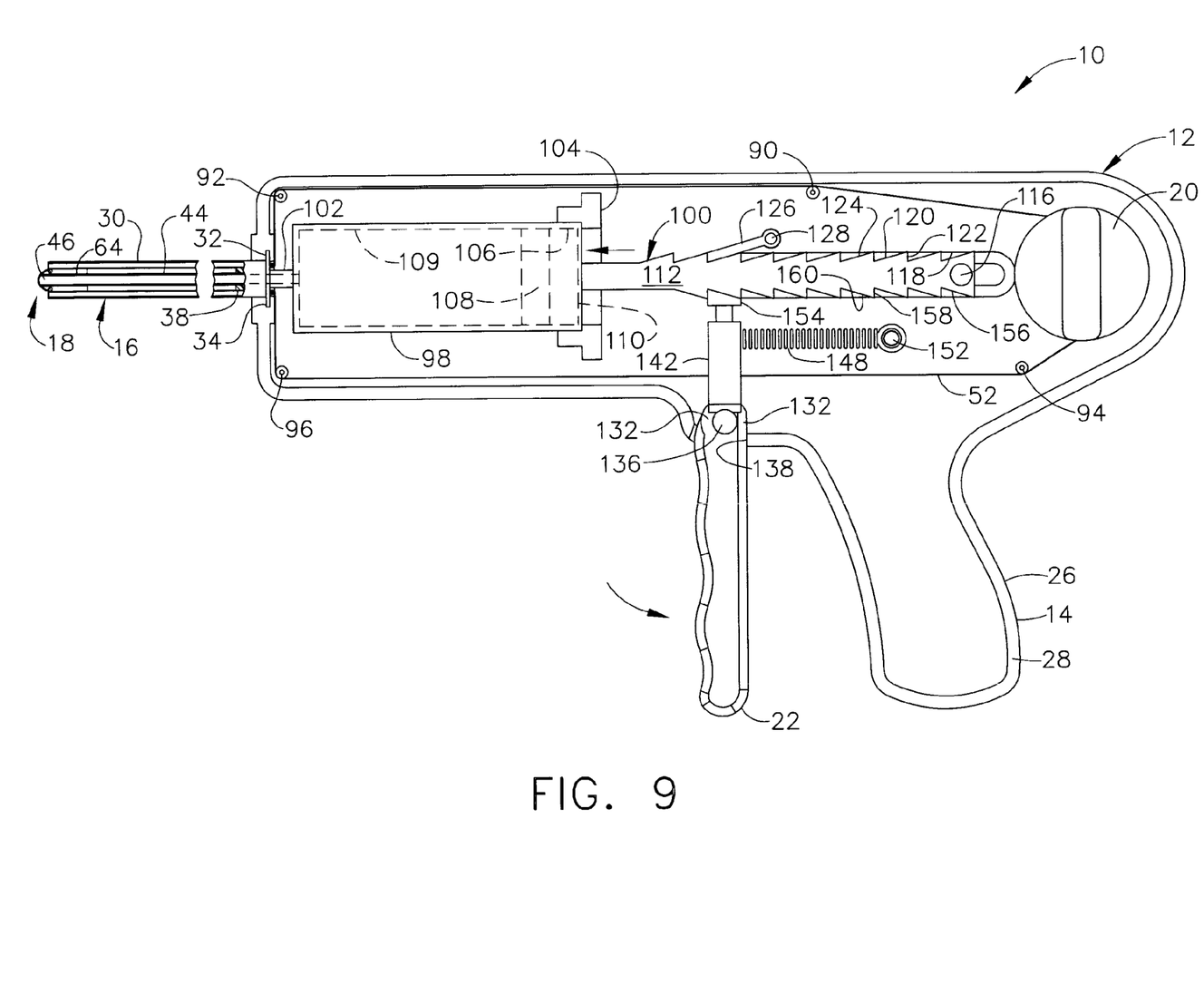
FIG. 9 is a left side view in elevation of the multiple use fluid dispenser of FIG. 1 with the left housing half shell and portions of the shaft removed as the first dispensing stroke concludes and an anti-backup engages a plunger arm.

In FIG. 9, the trigger 22 has reached its proximal most position as limited by the trigger aperture 138 in the housing 12, corresponding to a position in which the anti-backup pawl 126 drops into a second distal most position of the upper rack 120, holding the plunger 100 at this position.

Figure 10:
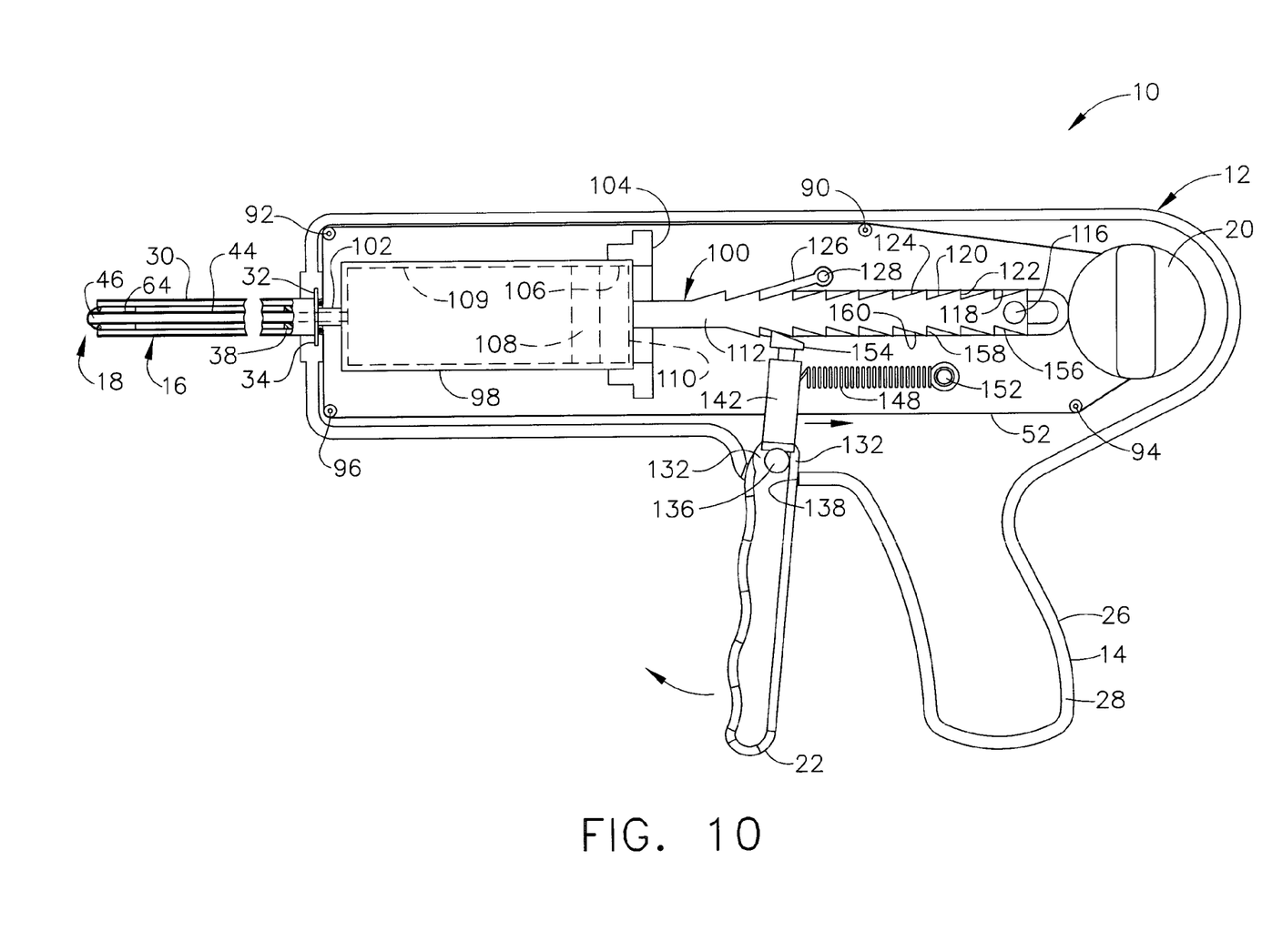
FIG. 10 is a left side view in elevation of the multiple use fluid dispenser of FIG. 1 with the left housing half shell and portions of the shaft removed as the trigger is released and the anti-backup pawl maintains a position of the plunger arm.

In FIG. 10, the trigger 22 is released, thus moving forward under the released energy stored in the compression spring 148 while the syringe volume 109 is maintained.

Figure 11:
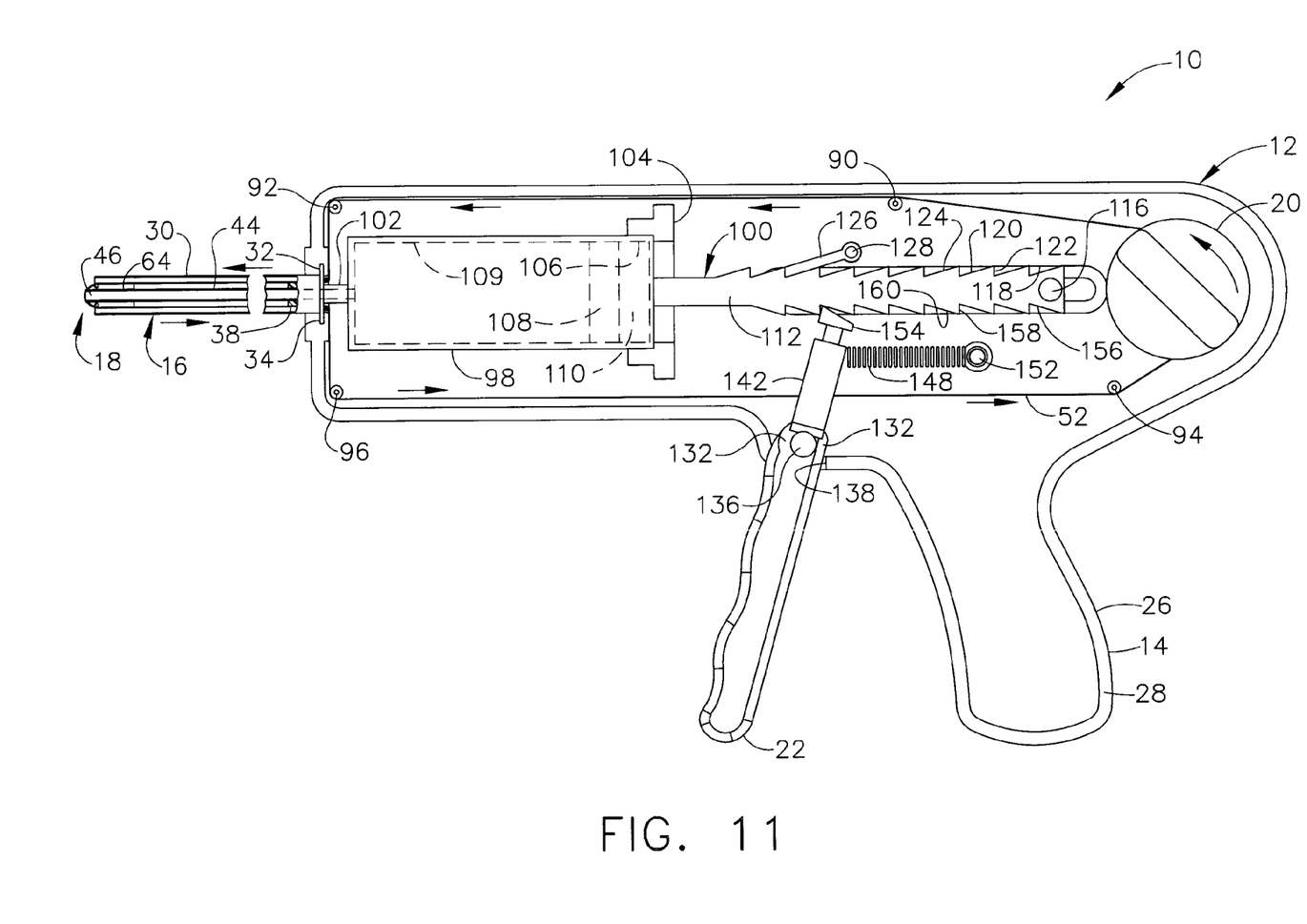
FIG. 11 is a left side view in elevation of the multiple use fluid dispenser of FIG. 1 with the left housing half shell and portions of the shaft removed as the trigger engages a second position of the plunger arm and an advancement knob is rotated to a next nondispensing position to prevent leakeage or clogging or is further rotated to a next dispensing position in preparation for a second dispensing stroke.

In FIG. 11, the trigger 22 has reached its fully forward relaxed position as allowed by the trigger aperture 139 in the housing 12. This position corresponds to the cam member 154 engaging a second distal most position of the lower rack 156 of the ratcheting plunger arm 112 positioned for a second dispensing stroke. The anti-backup pawl 126 remains engaged to the upper rack 120 until such second dispensing stroke. The advancement knob 20 is rotated to position the band 52 to either a non-dispensing position that may seal and/or wipe the dispensing orifice 46 of the fluid conduit 44 or position the band 52 to a dispensing position in preparation for the second dispensing stoke.

Figure 12:
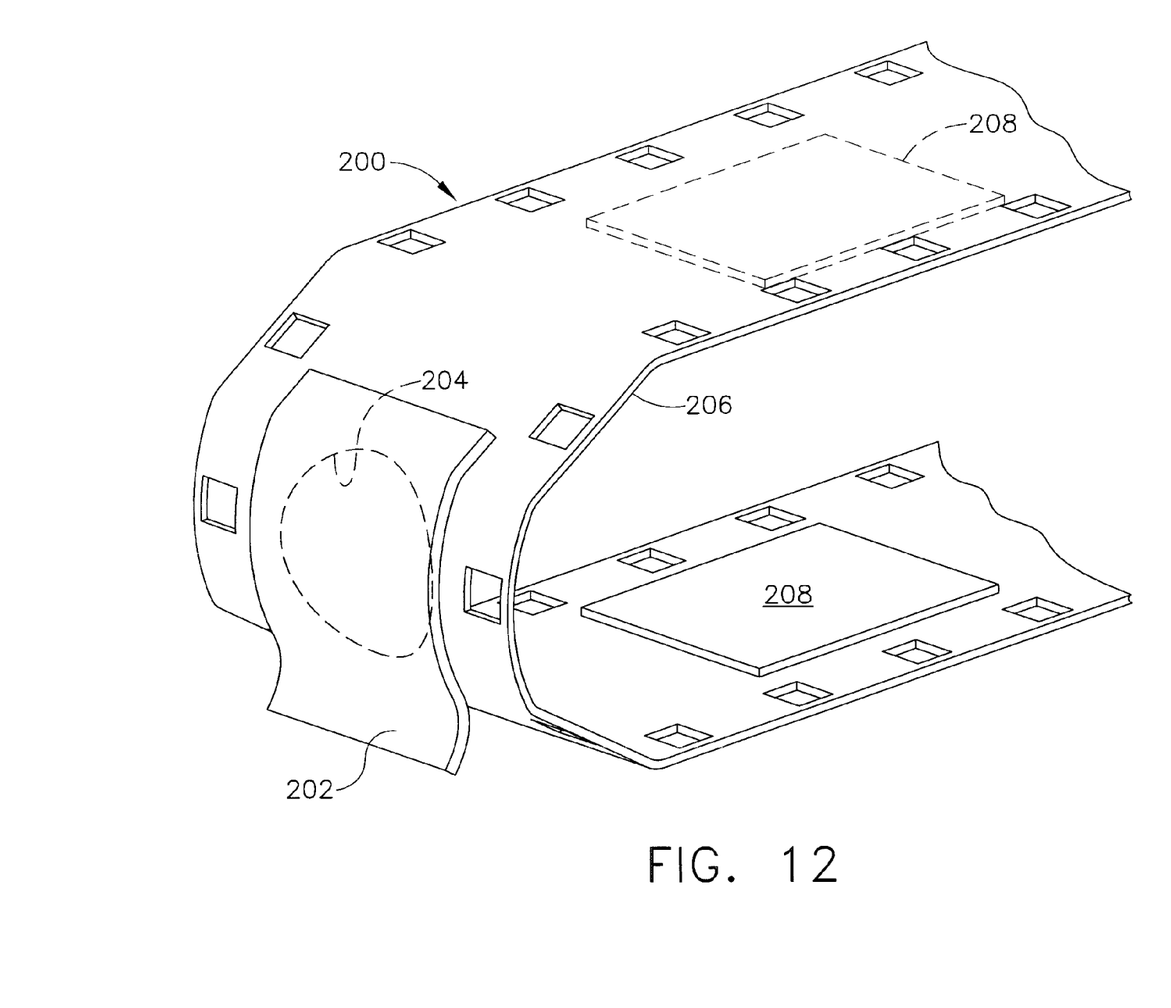
FIG. 12 is a front left detail isometric view of an alternative band having detachable outer band layers for the multiple use fluid dispenser of FIG. 1.
Figure 13:
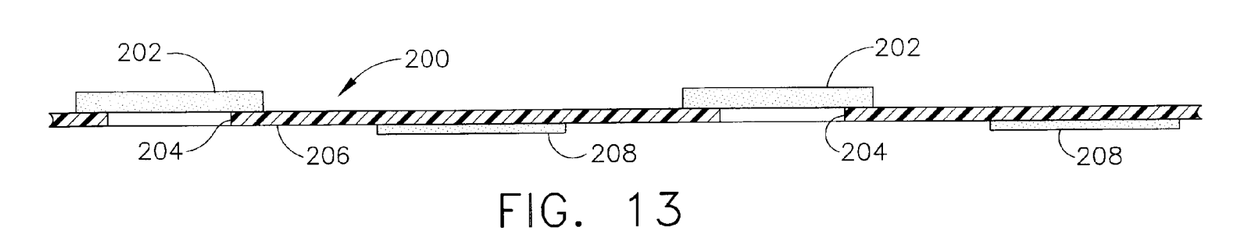
FIG. 13 is a side view of the alternative band of FIG. 12.

In FIGS. 12-13, an alternative band 200 for the multiple use fluid dispenser 10 of FIG. 1 includes detachable outer band layers 202 over a respective circular hole 204 formed sequentially in a band substrate 206 that may serve as a bandage or buttressing material or an initiation site for the polymerization of dispensed flowable material. Inner band layers 208 are equidistantly spaced between circular holes 204 on an inner surface of the band substrate 206 for providing a non-dispensing position that mitigates premature activation, leaking, clogging, etc.

Figure 14:
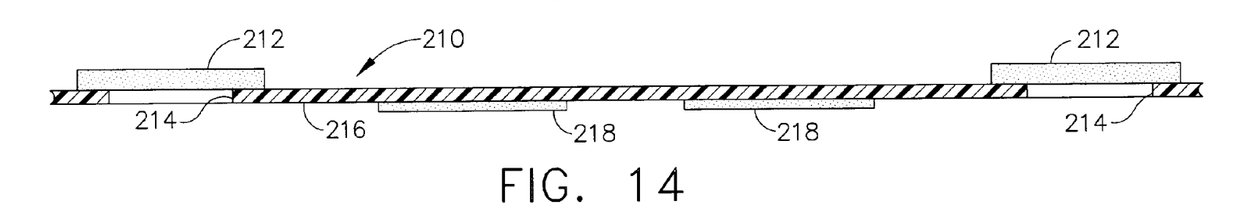
FIG. 14 is a side view of another alternative band for the multiple use fluid dispenser of FIG. 1 having two sequential non-dispensing positions.

In FIG. 14, another alternative band 210 for the multiple use fluid dispenser 10 of FIG. 1 includes outer band layers 212 over a respective circular hole 214 formed in a band substrate 216 and with two inner band layers 216 equidistantly spaced on an inner surface of a band substrate 216 for serving a first wiping surface followed by a clean sealing surface to further mitigate the likelihood of sticking or clogging between dispensing strokes.

Figures 15, 16:
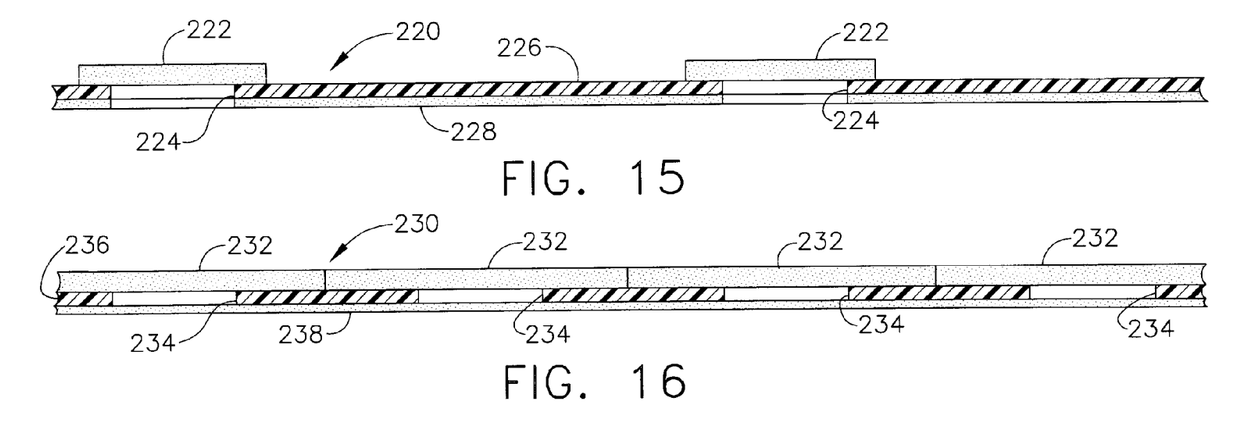
FIG. 15 is a side view of an additional alternative band for the multiple use fluid dispenser of FIG. 1 having an inner band layer removed at each dispensing.
FIG. 16 is a side view of a further alternative band for the multiple use fluid dispenser of FIG. 1 having a continuous inner band layer and a segmented continuous outer band layer.

In FIG. 15, an additional alternative band 220 for the multiple use fluid dispenser 10 of FIG. 1 includes outer band layers 222 over a respective circular hole 224 formed in a band substrate 226 and with a continuous inner band layer 228 which covers an inner surface of the band substrate 226 except for the circular holes 224 for serving as a continuous wiping and sealing surface to further mitigate the likelihood of sticking or clogging between dispensing strokes.

In FIG. 16, a further alternative band 230 for the multiple use fluid dispenser 10 of FIG. 1 includes adjacent outer layers 232 over a respective, half-spaced circular hole 234 formed in a band substrate 236 and with a continuous and porous inner band layer 238 covering an inner surface of the band substrate 236 except for the circular holes 234 for serving as a dispersal mesh, continuous wiping and sealing surface to further mitigate the likelihood of sticking or clogging between dispensing strokes.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For clarity, it should be appreciated that a simplified tip has been depicted that may have particular advantages for open or topical surgical procedures. It should be appreciated that various modifications may be made such as making flexible or deformable or articulating shaft for increased flexibility in endoscopic or laparoscopic surgical procedures. Various pneumatic sealing features may be incorporated to assist in maintaining an insufflated body cavity for laparoscopic procedures.

It should be appreciated with the benefit of the present disclosure that terms such as fluid are intended to encompass a range of medically therapeutic flowable materials, to include emulsions, mixtures of liquids and solids, etc. Furthermore, for clarity, certain applicator tips have been illustrated; however, applicator tips consistent with aspects of the present invention may include various opening patterns, to include shape in a dispensing band may be employed, optimized for a given viscosity or other property of the dispensed flowable material.

As another example, applications consistent with the present invention may employ another type of fluid transfer apparatus to urge a pressurized volume of flowable material toward a distal dispensing orifice, such as a gas charged or spring biased plunger. A trigger or similar actuator may effect dispensing solely by rotation of the band to a position in which the flowable material is allowed to extrude out under inherent pressure. When dispensing is to conclude, reposition of the trigger, such as to a release state, rotates the band to a blocked, sealed position. Such rotation of the band may be reciprocating or looping in a constant direction depending on the characteristics of the flowable material.

As yet another example, applications consistent with the present invention may employ a tape that does not loop, but instead is unreeled from a storage reel, routed past a distal dispensing orifice and then reeled up on a take-up reel. Alternatively, a substrate may comprise a continuous loop but also include an intermediate storage reel similar to an 8-track cassette.

As yet a further example, while sprocket holes enhance positive positioning of the substrate, applications consistent with the present invention may employ a frictionally engaged substrate transport mechanism.

As another example, applications consistent with aspects of the present invention may include a visual indicator that alerts the user as to the remaining number or quantity of flowable material remaining or already dispensed and/or the number of dispensing operations allowable by the amount of unused band remaining. Furthermore, a lockout may seal off further dispensing once the band is exhausted of initiator layers or detachable layers.

As yet another example, while a multiple stroke trigger is illustrated, applications consistent with the present invention may include a single stroke trigger or a rotated actuator or a manually pushed syringe plunger.

What is claimed is:

1. A dispenser for a surgical procedure, comprising:
   (a) a handle;
   (b) an elongate shaft, the elongate shaft being connected to the handle for positioning the elongate shaft;
   (c) a dispensing orifice associated with the elongate shaft;
   (d) a fluid transfer apparatus operably configured to urge a flowable material to the dispensing orifice, wherein the fluid transfer apparatus comprises:
      (i) a syringe,
      (ii) a syringe barrel containing a volume of the flowable material,
      (iii) a syringe plunger received in the syringe barrel to expel the flowable material,
      (iv) an anti-backup mechanism coupled to the syringe plunger to prevent retraction of the syringe plunger, and
      (v) an actuator operably coupled to selectively advance the syringe plunger;
   (e) a substrate overlying the dispensing orifice, the substrate having a dispensing opening,
      wherein the substrate forms part of a band, the band further comprising an outer band layer, a first inner band layer, and a second inner band layer,
      wherein the outer band layer is attached to the substrate and is sized to cover the dispensing opening,
      wherein the first inner band layer comprises a wiping surface, and
      wherein the second inner band layer comprises a clean sealing surface; and
   (f) a substrate transport mechanism operably configured to selectively offset the dispensing opening in the substrate from the dispensing orifice and to align the dispensing opening in the substrate with the dispensing orifice.

2. The dispenser of claim 1, the substrate transport mechanism comprising a rotation wheel in partial circumferential contact with the band, the substrate transport mechanism being further operably configured to rotate the band in a selected direction to avoid returning a previously aligned portion of the band to the dispensing orifice.

3. The dispenser of claim 1, wherein the substrate further comprises a series of sprocket holes, the substrate transport mechanism comprising a sprocket wheel engaged to the series of sprocket holes.

4. The dispenser of claim 1, wherein the flowable material comprises an adhesive compound reactive to an initiator, the outer layer comprising a porous material containing the initiator.

5. The dispenser of claim 1, wherein the outer band layer comprises a releasable attachment to the substrate for deposition during dispensing of the flowable material.

6. The dispenser of claim 1, wherein at least one of the first or second inner band layers are positioned to contact the dispensing orifice when the substrate transport mechanism offsets the position of the dispensing opening of the substrate from the dispensing orifice.

7. The dispenser of claim 1, wherein the actuator comprises a trigger pivotally attached relative to the elongate shaft, wherein the actuator further comprises a cam member extending into the handle from the trigger to engage the syringe plunger.

8. The dispenser of claim 1, further comprising: a fluid conduit in fluid communication between the syringe barrel and the dispensing orifice, wherein the substrate is looped on both sides of a length of the fluid conduit, wherein the elongate shaft forms an outer tube encompassing the looped length of the substrate and the length of the fluid conduit.

9. The dispenser of claim 1, wherein said outer band layer comprises a mesh permanently attached to said band substrate.

10. The dispenser of claim 1, wherein the band forms a loop.

11. The dispenser of claim 1, wherein the first and second inner band layers are equidistantly spaced on an inner surface of the band substrate.

12. A dispenser for a surgical procedure, comprising:
   (a) a handle;
   (b) an elongate shaft coupled with the handle;
   (c) a dispensing orifice associated with the elongate shaft;
   (d) a fluid transfer apparatus operably configured to urge a flowable material to the dispensing orifice;
   (e) a substrate overlying the dispensing orifice, the substrate having a dispensing opening,
      wherein the substrate forms part of a band, the band further comprising an outer band layer, a first inner band layer, and a second inner band layer,
      wherein the outer band layer is attached to the substrate and is sized to cover the dispensing opening,
      wherein the first inner band layer comprises a wiping surface, and
      wherein the second inner band layer comprises a clean sealing surface; and
   (f) a substrate transport mechanism operably configured to selectively offset the dispensing opening in the substrate from the dispensing orifice and to align the dispensing opening in the substrate with the dispensing orifice.

13. The dispenser of claim 12, wherein the fluid transfer apparatus comprises:
   (i) a syringe,
   (ii) a syringe barrel containing a volume of the flowable material,
   (iii) a syringe plunger received in the syringe barrel to expel the flowable material,
   (iv) an anti-backup mechanism coupled to the syringe plunger to prevent retraction of the syringe plunger, and
   (v) an actuator operably coupled to selectively advance the syringe plunger.

14. A dispenser for a surgical procedure, comprising:
(a) a handle;
(b) an elongate shaft coupled with the handle;
(c) a dispensing orifice associated with the elongate shaft;
(d) a fluid transfer apparatus operably configured to urge a flowable material to the dispensing orifice;
(e) a band, wherein the band comprises:
  (i) a substrate overlying the dispensing orifice, the substrate having a plurality of dispensing openings;
  (ii) an outer band layer, wherein the outer band layer is attached to the substrate and is sized to cover at least one of the dispensing openings;
  (iii) a first inner band layer, wherein the first inner band layer comprises a wiping surface;
(f) a substrate transport mechanism operably configured to selectively offset the dispensing opening in the substrate from the dispensing orifice and to align the dispensing opening in the substrate with the dispensing orifice; and
(g) wherein the band further comprises a second inner band layer, said second inner band layer comprises a clean sealing surface.

* * * * *